United States Patent
Lane, II

(10) Patent No.: US 11,278,786 B2
(45) Date of Patent: Mar. 22, 2022

(54) SYSTEM AND METHOD FOR INCENTIVIZING AND QUANTIFYING PATIENT MOBILITY

(71) Applicant: Hill-Rom Services, Inc., Batesville, IN (US)

(72) Inventor: Timothy A. Lane, II, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 252 days.

(21) Appl. No.: 16/553,271

(22) Filed: Aug. 28, 2019

(65) Prior Publication Data
US 2020/0101364 A1 Apr. 2, 2020

Related U.S. Application Data

(60) Provisional application No. 62/738,131, filed on Sep. 28, 2018.

(51) Int. Cl.
*A63B 71/06* (2006.01)
*A63B 24/00* (2006.01)

(52) U.S. Cl.
CPC ...... *A63B 71/0622* (2013.01); *A63B 24/0062* (2013.01); *A63B 24/0075* (2013.01); *A63B 2071/0675* (2013.01); *A63B 2208/0233* (2013.01); *A63B 2208/0242* (2013.01); *A63B 2220/58* (2013.01); *A63B 2225/20* (2013.01)

(58) Field of Classification Search
CPC .............................. A63B 71/0622; G16H 20/03
See application file for complete search history.

(56) References Cited

U.S. PATENT DOCUMENTS

| | | | |
|---|---|---|---|
| 5,626,537 A | 5/1997 | Danyo et al. | |
| 7,328,119 B1 | 2/2008 | Pryor et al. | |
| 7,822,472 B1 | 10/2010 | Xi | |
| 8,177,732 B2 * | 5/2012 | Einav | A63B 21/012 601/5 |

(Continued)

FOREIGN PATENT DOCUMENTS

| | | |
|---|---|---|
| EP | 1850824 B1 | 7/2006 |
| KR | 20170086793 A | 7/2017 |

(Continued)

OTHER PUBLICATIONS

Ellinor K. Olandero et al., "What are the most effective techniques in changing obese individuals' physical activity self-efficacy and behaviour: a systematic review and meta-analysis," International Journal of Behavioral Nutrition and Physical Activity, vol. 10(29), Mar. 3, 2013, 15 pages.

(Continued)

*Primary Examiner* — Joshua Lee
(74) *Attorney, Agent, or Firm* — Barnes & Thornburg LLP

(57) ABSTRACT

A patient support apparatus includes a controller having a processor and a memory. The memory may have instructions stored therein related to an exercise regimen for a patient. A graphical user interface may be provided. The controller may be configured to display an alert on the graphical user interface when the patient requires exercise. User inputs may be displayed on the graphical user interface to enable a caregiver to record exercises completed by the patient.

18 Claims, 6 Drawing Sheets

(56) References Cited

U.S. PATENT DOCUMENTS

| | | |
|---|---|---|
| 9,038,218 B1 | 5/2015 | Heil et al. |
| 2003/0211916 A1 | 11/2003 | Capuano |
| 2008/0119763 A1 | 5/2008 | Wiener |
| 2009/0287103 A1 | 11/2009 | Pillai |
| 2012/0259648 A1 | 10/2012 | Mallon et al. |
| 2012/0295240 A1 | 11/2012 | Walker et al. |
| 2013/0123667 A1 | 5/2013 | Komatireddy et al. |
| 2014/0081661 A1 | 3/2014 | Fu et al. |
| 2014/0206503 A1 | 7/2014 | Stockmaster et al. |
| 2014/0330408 A1* | 11/2014 | Rolley ............... G06K 9/00288 700/91 |
| 2015/0134088 A1* | 5/2015 | Romeo ................. G16H 20/30 700/91 |
| 2015/0141203 A1 | 5/2015 | Ohlsen |
| 2016/0143593 A1* | 5/2016 | Fu ........................... A61B 5/11 600/595 |
| 2016/0271452 A1* | 9/2016 | Lagree ............... A63B 22/0076 |
| 2016/0314277 A1 | 10/2016 | Korhonen et al. |
| 2017/0293742 A1* | 10/2017 | Sadeghi ................. G16H 50/50 |

FOREIGN PATENT DOCUMENTS

| | | |
|---|---|---|
| WO | 0045897 A1 | 8/2000 |
| WO | 2005074369 A2 | 8/2005 |
| WO | 2006061834 A2 | 6/2006 |

OTHER PUBLICATIONS

Extended European Search Report for Application No. 19197275.1 dated Feb. 20, 2020, 8 pages.

\* cited by examiner

FIG. 6

SYSTEM AND METHOD FOR INCENTIVIZING AND QUANTIFYING PATIENT MOBILITY

CROSS-REFERENCE TO RELATED APPLICATIONS

This application claims priority under 35 U.S.C. § 119(e) to U.S. Provisional Patent Application Ser. No. 62/738,131, filed Sep. 28, 2018, which is expressly incorporated by reference herein.

BACKGROUND

The present disclosure relates to a system and method to incentivize patient mobility. More specifically, the present disclosure relates to ensuring the completion of a patient exercise regimen.

Mobility is a significant contributor to patient recovery. Unfortunately, following a recovery or exercise regimen is difficult for patients when they are not feeling well. In some cases patients may not know or remember what they can do to help their recovery.

There are two key contributors to improve mobility in the med-surg environment: activating the nurse, and engaging the family. Both can be accomplished with two steps: monitoring mobility progression towards a daily goal, and displaying the information to nurses and family. Mobility progression is fairly consistent hospital to hospital, and may involve the following: time head is elevated, time patient side-sits, number of bed exits and entries, distance walked, cycles of alternate leg lifts, time spent out of bed, etc. The nurse or physical therapist can pre-select the daily goals for the patient, and score their progress based on first-hand observations or verbal feedback from the patient, family, or other caregivers. The second step is more difficult, displaying the information in a way that activates the nurse and engages the family. The primary goal is to engage the family, but nurses also contribute to ensuring that the patient is exercising.

SUMMARY

The present disclosure includes one or more of the features recited in the appended claims and/or the following features which, alone or in any combination, may comprise patentable subject matter.

According to one aspect of the disclosed embodiments, a patient support apparatus includes a controller having a processor and a memory. The memory may have instructions stored therein related to an exercise regimen for a patient. A graphical user interface may be provided. The controller may be configured to display an alert on the graphical user interface when the patient is scheduled to exercise. User inputs may be displayed on the graphical user interface to enable a caregiver to record exercises completed by the patient. The processor may be configured to compare the exercises completed by the patient to the exercise regimen. The graphical user interface may display a chart of the exercises completed relative to the exercise regimen.

In some embodiments, the processor may be configured to update the exercise regimen based on a comparison of the exercises completed to the exercise regimen.

Optionally, the controller may send an alert to a remote computer when the patient is scheduled to exercise.

It may be desired that the remote computer is at a nurse's station. The remote computer may be a mobile device. The controller may send updates to a remote computer related to the exercises completed. The remote computer may be at least one of a nurse's computer, a doctor's computer, or a therapist's computer.

Alternatively or in addition to, the patient support apparatus may be a hospital bed or a patient chair.

It may be contemplated that the alert is a text message or a light. The controller may provide an audible alert when the patient is scheduled to exercise.

In some embodiments, the graphical user interface may have a keypad to enter the exercises completed. The keypad may be a touch-screen display.

Optionally, the exercise regimen includes sitting in a chair position on the patient support apparatus, range of motion exercises, participating in self-care, in-bed strengthening, sitting up in a chair with maximum assistance, dangling legs from the patient support apparatus, showering in a chair, moving to a sink for self-care, sitting up in a chair with minimum assistance, or walking. The exercise regimen may include a number of sets of the exercise and a number of repetitions per set.

It may be desired that load cells provide signals indicative of movement of the patient on the patient support apparatus during exercise.

According to another embodiment of the disclosed embodiments, a method of rehabilitating a patient may include storing an exercise regimen for the patient in the memory of a controller at a patient support apparatus. The exercise regime may include predetermined times for the patient to exercise. The method may also require displaying an alert of a graphical user interface at the predetermined times. The method may also require recording data related to exercises performed in the memory of the controller.

In some embodiments, the method may require comparing the data related to the exercises performed to the exercise regimen. The method may also require updating the exercise regimen based on a comparison of the data related to the exercises performed to the exercise regimen. The method may also require displaying a chart comparing the exercises performed and the exercise regimen.

Optionally, the method may require displaying the alert on a remote device.

It may be contemplated that the exercise regimen includes at least one of sitting in a chair position on a patient support apparatus, range of motion exercises, participating in self-care, in-bed strengthening, sitting up in a chair with maximum assistance, dangling legs from the patient support apparatus, showering in a chair, moving to a sink for self-care, sitting up in a chair with minimum assistance, or walking.

Optionally, the method may require tracking movement of the patient based on signals from at least one load cell.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which:

FIG. 6 is a screen shot of an exercise goal screen displaying a chart that tracks the patient's exercise.

DETAILED DESCRIPTION

Figure 1:
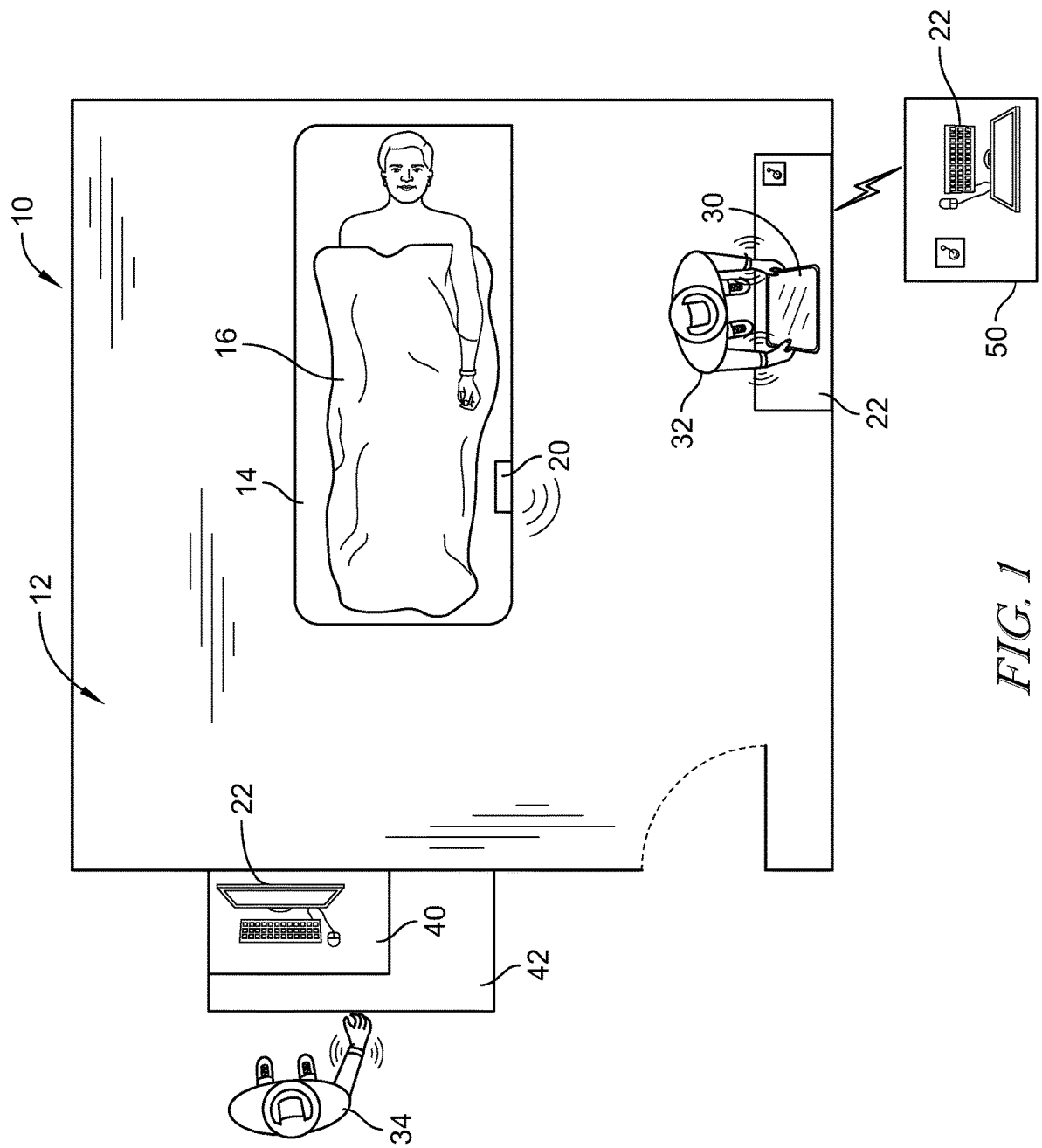
FIG. 1 is a plan view showing a patient room in a healthcare facility including a patient support apparatus and various computers.

Referring to FIG. 1, a healthcare facility 10 includes a number of patient rooms 12. For simplicity, only one patient room 12 is illustrated. The patient room 12 includes a patient support apparatus 14 for long term care of a patient 16. In the illustrative embodiment, the patient support apparatus 14 is a hospital bed; however, in other embodiments, the patient support apparatus 14 may be a patient chair, a chair-bed, or any other apparatus for supporting a patient 16.

The patient support apparatus 14 includes a controller 20 configured to control operation of the patient support apparatus 14, for example, raising and lowering sections of the patient support apparatus 14. The controller 20 is in communication with a plurality of remote devices 22. The controller 20 may be hardwired to the remote devices 22 or may communicate with the remote devices 22 through a wireless connection. The controller 20 is configured to send data to the remote devices 22, for example, patient alerts or patient updates. In some embodiments, the patient support apparatus 14 may be remotely operable by sending commands from the remote devices 22 to the controller 20.

In the illustrative embodiment, the remote devices 22 include a family device 30. The family device 30 may be a handheld device such as a tablet or a phone. In some embodiments, the patient's family may be provided with the family device 30 when the patient is checked in to the healthcare facility 10. In other embodiments, the family device 30 may be a personal device of a family member that is registered with the healthcare facility 10. The family device 30 includes a display that enables a family member 32 to receive updates and alerts regarding the patient 16. For example, as described herein, the family member 32 may receive alerts related to the necessary exercises for the patient 16. The family member 32 may also receive alerts that the patient 16 requires medication or that the patient 16 is in need of attention. By alerting the family member 32, the family member 32 can ensure that a caregiver 34 is notified of the alerts. Although the family device 30 is illustrated in the patient room 12, it will be appreciated that the family device 30 may be operable from any location in the healthcare facility 10.

The remote devices 22 also include a nurse device 40 that may be a mobile device or a computer located at a nurse's station 42. The controller 20 is configured to send alerts regarding the patient 16 to the nurse device 40 to notify the caregiver 34 of patient needs, for example exercise or medication. By sending alerts to both the nurse device 40 and the family device 30, redundancy is provided in the alerts sent by the controller 20. In some embodiments, only certain alerts may be sent to one of the nurse device 40 or the family device 30. For example, alerts regarding patient medication may only be sent to the nurse device 40.

The remote devices 22 also include a physician or therapist device 50. As described in more detail below, the controller 20 may send alerts to the device 50 regarding an exercise regimen of the patient 16. For example, the doctor or therapist may be updated on which exercises the patient 16 has performed at a given time on a given day. Accordingly, the doctor or therapist can track the patient's progress in recovery based on the patient's ability to complete certain exercises. It will be appreciated that the doctor or therapist may also receive other alerts, for example, updates on medication administered to the patient 16. The doctor or physician may update the patient's medical record based on the alerts. In some embodiments, the controller 20 may also send alerts and updates to an electronic medical record, for example an electronic medical record at the nurse device 40 or the device 50 to automatically update the patient's medical record.

Figure 2:
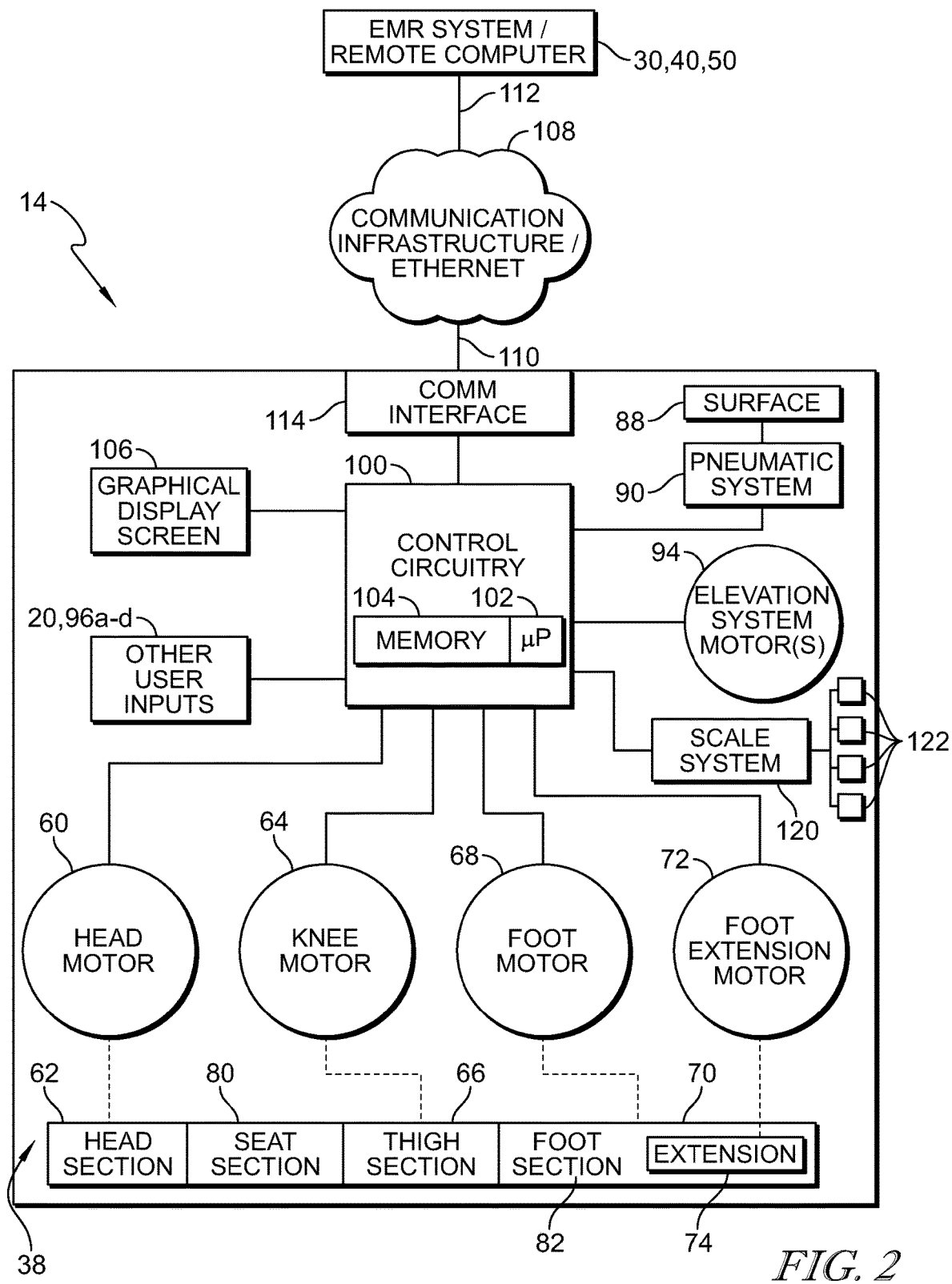
FIG. 2 is a block diagram showing electrical circuitry of the patient support apparatus in communication with a remote computer of an EMR system.

As shown diagrammatically in FIG. 2, patient support apparatus 14 includes a head motor or actuator 60 coupled to a head section 62, a knee motor or actuator 64 coupled to a thigh section 66, a foot motor or actuator 68 coupled to a foot section 70, and a foot extension motor or actuator 72 coupled to foot extension 74. Motors 60, 64, 68, 72 may include, for example, an electric motor of a linear actuator. In those embodiments in which seat section 80 translates along an upper frame, a seat motor or actuator (not shown) is also provided. Head motor 60 is operable to raise and lower head section 62, knee motor 64 is operable to articulate thigh section 66 relative to seat section 80, foot motor 68 is operable to raise and lower foot section 70 relative to thigh section 66, and foot extension motor 72 is operable to extend and retract extension 74 of foot section 70 relative to main portion 82 of foot section 70.

In some embodiments, patient support apparatus 14 includes a pneumatic system 90 that controls inflation and deflation of various air bladders or cells of a mattress 88 of the patient support apparatus 14. The pneumatic system 90 is represented in FIG. 2 as a single block but that block 90 is intended to represent one or more air sources (e.g., a fan, a blower, a compressor) and associated valves, manifolds, air passages, air lines or tubes, pressure sensors, and the like, as well as the associated electric circuitry, that are typically included in a pneumatic system for inflating and deflating air bladders of mattresses.

As also shown diagrammatically in FIG. 2, a lift system of patient support apparatus 14 includes one or more elevation system motors or actuators 94, which in some embodiments, comprise linear actuators with electric motors. Thus, actuators 94 are sometimes referred to herein as motors 94. Alternative actuators or motors contemplated by this disclosure include hydraulic cylinders and pneumatic cylinders, for example. The motors 94 of lift system 92 are operable to raise, lower, and tilt an upper frame assembly relative to a base. In the illustrative embodiment, one of motors 94 is coupled to, and acts upon, a set of head end lift arms and another of motors 94 is coupled to, and acts upon, a set of foot end lift arms to accomplish the raising, lowering and tilting functions of the upper frame relative to the base.

In the illustrative example, patient support apparatus 14 has four foot pedals 96a, 96b, 96c, 96d. Foot pedal 96a is used to raise the upper frame assembly relative to the base, foot pedal 96b is used to lower the frame assembly relative to the base, foot pedal 96c is used to raise head section 60 relative to the frame, and foot pedal 96d is used to lower head section 60 relative to the frame. In other embodiments, foot pedals 96a-d are omitted.

Control panel 20 includes various buttons that are used by a caregiver (not shown) to control associated functions of patient support apparatus 14. For example, control panel 20 includes buttons that are used to operate head motor 62 to raise and lower the head section 60, buttons that are used to operate knee motor 66 to raise and lower the thigh section 64, and buttons that are used to operate motors 94 to raise, lower, and tilt the upper frame assembly relative to base. In the illustrative embodiment, control panel 20 includes buttons that are used to operate motor 68 to raise and lower foot section 70 and buttons that are used to operate motor 72 to extend and retract foot extension 70 relative to main portion 82. In some embodiments, the buttons of control panels 20 include membrane switches. In some embodiments, the buttons of control panel 20 include touch-screen icons.

As shown diagrammatically in FIG. 2, patient support apparatus 14 includes control circuitry 100 that is electrically coupled to motors 60, 64, 68, 72 and to motors 94 of lift system 92. Control circuitry 100 is represented diagrammatically as a single block 60 in FIG. 2, but control circuitry 100 in some embodiments comprises various circuit boards, electronics modules, and the like that are electrically and communicatively interconnected. Control circuitry 100 includes one or more microprocessors 102 or microcontrollers that execute software to perform the various control functions and algorithms described herein. Thus, circuitry 100 also includes memory 104 for storing software, variables, calculated values, and the like as is well known in the art.

As also shown diagrammatically in FIG. 2, a user inputs block represents the various user inputs such as buttons of the control panel 20 and pedals 96a-d, for example, that are used by the caregiver or patient to communicate input signals to control circuitry 100 of patient support apparatus 14 to command the operation of various motors 60, 64, 68, 72 of patient support apparatus 14, as well as commanding the operation of other functions of patient support apparatus 14. Patient support apparatus 14 includes at least one graphical user input or display screen 106. Display screen 106 is coupled to control circuitry 100 as shown diagrammatically in FIG. 2. In some embodiments, two graphical user interfaces 106 are provided. Alternatively or additionally, one or more graphical user interfaces are coupled to the siderails and/or to one or both of the headboard and footboard of patient support apparatus 14. Control circuitry 100 receives user input commands from graphical display screen 106.

According to this disclosure, control circuitry 100 of patient support apparatus 14 communicates with the remote devices 30, 40, and 50 via communication infrastructure 108 such as an Ethernet of the healthcare facility 10 in which patient support apparatus 14 is located and via communications links 110, 112 as shown diagrammatically in FIG. 2. Remote computers 40 and 50 are part of an electronic medical records (EMR) system according to this disclosure. However, it is within the scope of this disclosure for circuitry 100 of patient support apparatus 14 to communicate with other computers such as those included as part of a nurse call system, a physician ordering system, an admission/discharge/transfer (ADT) system, or some other system used in a healthcare facility in other embodiments. Ethernet 108 in FIG. 2 is illustrated diagrammatically and is intended to represent all of the hardware and software that comprises a network of a healthcare facility.

In the illustrative embodiment, patient support apparatus 14 has a communication interface or port 114 which provides bidirectional communication via link 116 with infrastructure 108 which, in turn, communicates bidirectionally with computers 30, 40, 50 via link 110. Link 110 is a wired communication link in some embodiments and is a wireless communications link in other embodiments. Thus, communications link 110, in some embodiments, comprises a cable that connects patient support apparatus 14 to a wall mounted jack that is included as part of a bed interface unit (BIU) or a network interface unit (NIU). In other embodiments, communications link 110 comprises wireless signals sent between patient support apparatus 14 and a wireless interface unit of the type shown and described in U.S. Patent Application Publication No. 2007/0210917 A1 which is hereby expressly incorporated by reference herein. Communications link 112 comprises one or more wired links and/or wireless links as well according to this disclosure.

As mentioned above, patient support apparatus 14 includes EMR charting capability so that information can be charted into a patient's EMR via commands entered on patient support apparatus 14 without the need for subsequent confirmatory actions by personnel at remote computers. In some embodiments contemplated by this disclosure, subsequent confirmatory actions may be required at EMR system computer 40 or 50 prior to entry of data into a patient's EMR. However, systems in which information is charted or stored in a patient's EMR via caregiver actions at patient support apparatus 14 without the need for subsequent actions at remote computer 40 or 50 by the same or a different caregiver is seen as being more efficient.

Patient support apparatus 14 includes a scale system 120 as shown diagrammatically in FIG. 2. Scale system 120 includes one or more weight sensors that are indicative of the weight of the patient on patient support apparatus 14. In some embodiments, the scale system 120 includes four load cells 122 (e.g., load beams with strain gages) that interconnect a lift frame with a weigh frame adjacent the four corners of the frame. In addition to sensing an amount of weight of the patient, the data from the sensors of scale system 120 is also used by control circuitry 100 to determine the patient's position relative to patient support apparatus 14. Thus, in the illustrative example, data from the sensors of weigh scale system 120 is compared to thresholds associated with the Exiting, Out-of-Bed, and Patient Position modes of the PPM system to determine if an alarm condition exists. The scale system 120 may also be utilized to track movement of a patient during exercise.

The memory 104 includes instructions related to an exercise regimen for the patient 16. The instructions instruct the processor 102 to display alerts related to the exercise regimen on the graphical user interface 106. The instructions also instruct the processor 102 to send the alerts to at least one of the devices 30, 40, or 50. The user may enter a number of repetitions of an exercise performed and/or a number of sets of the exercise performed using the buttons of the graphical user interface 106.

The exercise regimen includes a plurality of exercises that the patient 16 is instructed to perform at various times in the day. For example, the exercises may include at least one of sitting in a chair position on patient support apparatus 14, range of motion exercises, participating in self-care, in-bed strengthening, sitting up in a chair with maximum assistance, dangling legs from the patient support apparatus 14, showering in a chair, moving to a sink for self-care, sitting up in a chair with minimum assistance, or walking. Each exercise may require a predetermined number of sets and/or a predetermined number of repetitions per set. The exercises may also be divided into phases as the patient 16 progresses. In a first phase, the exercises may include sitting in a chair position on patient support apparatus 14 and range of motion exercises. In a second phase, the exercises may include participating in self-care, in-bed strengthening, sitting up in a chair with maximum assistance and dangling legs from the patient support apparatus 14. In a third phase, the exercises may include showering in a chair, moving to a sink for self-care, sitting up in a chair with minimum assistance. In a fourth phase, the exercises may include walking, for example, walking the hallway of the healthcare facility 10. The instructions may include predetermined times that each exercise is to be performed.

Figure 3:
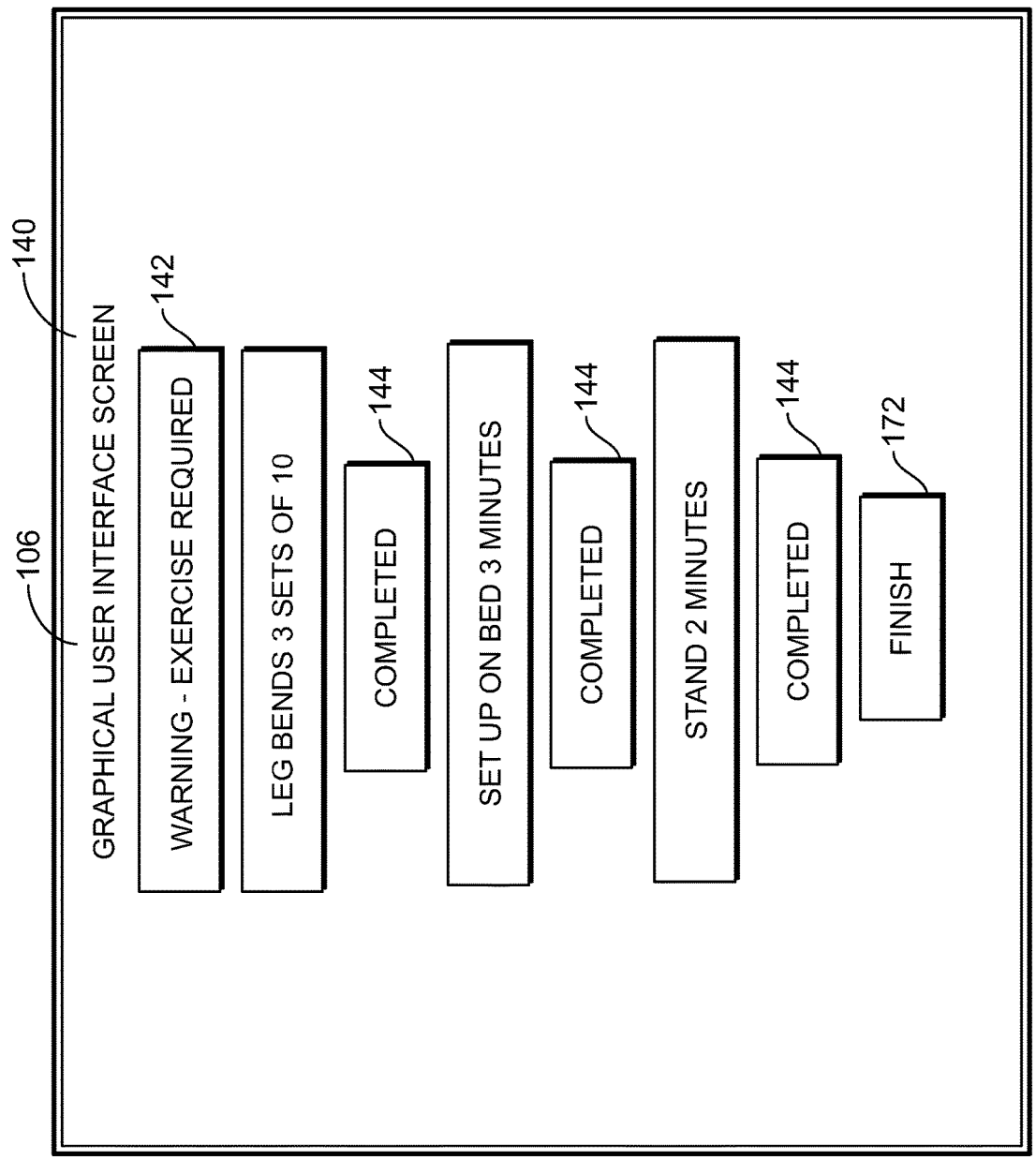
FIG. 3 is a screen shot of an exercise status screen showing an alert that the patient needs to exercise.

FIG. 3 illustrates an exemplary screen 140 that is displayed in the graphical user interface 106. The controller 20 may also send signals to at least one of the devices 30, 40, or 50 to display the screen 140 on an interface of the respective device 30, 40, 50. The screen 140 includes an alert 142 that the patient 16 is scheduled to do exercise. In some embodiments, the alert may include a text message, an audible sound, or a light. The controller 20 sends the signals regarding the alert 142 so that the screen 140 is displayed at the predetermined time that the exercise is scheduled. In the exemplary screen 140, the patient 16 is being instructed to perform leg bends, sit up on the bed for three minutes, and stand for two minutes. Each exercise, includes a "completed" icon 144 that may be selected either when the patient completes the exercise or when it is determined that the patient is unable to complete the exercise.

Figure 4:
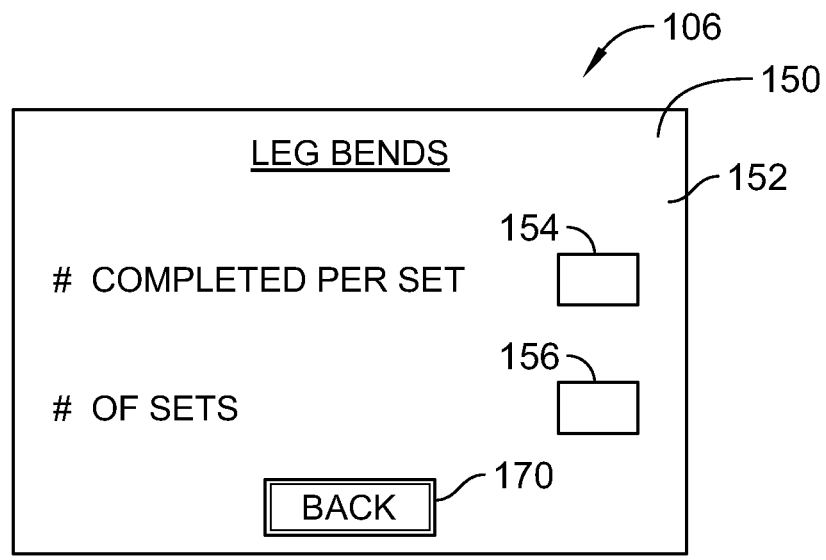
FIG. 4 is a screen shot of a first exercise input screen displaying fields for recording a patient leg bend exercise.
Figure 5:
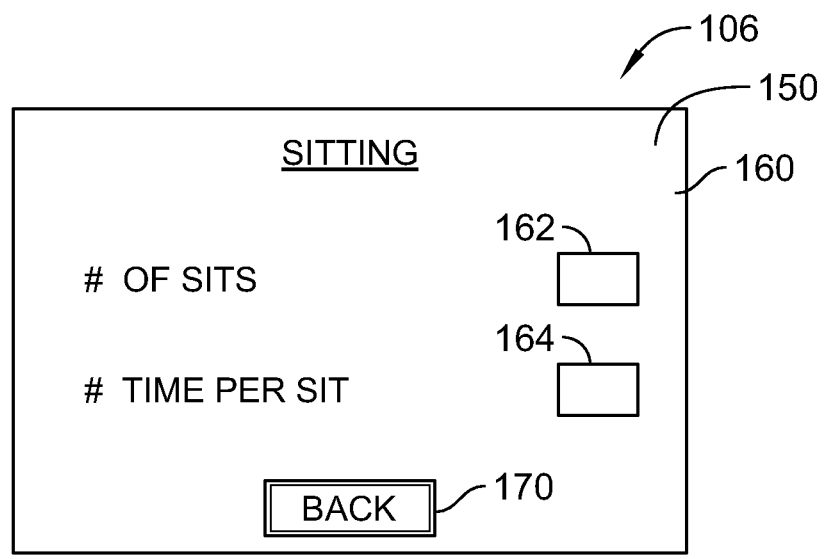
FIG. 5 is a screen shot of a second exercise input screen displaying fields for recording a patient sitting exercise.

By selecting the icon 144 an exercise screen 150 is displayed on the interface 106 or the interface of at least one of the devices 30, 40, or 50. FIGS. 4 and 5 illustrate examples of an exercise screen 150. For example, in the exercise screen 152 of FIG. 4, a user is requested to enter input regarding the patient's leg bend exercise. A set icon 154 enables the user to enter input regarding the number of leg bend sets completed, for example three sets. A repetition icon 156 enables the user to enter input regarding the number of repetitions the patient 16 performed in each set, for example 10 repetitions. In another example, in the exercise screen 160 of FIG. 5, the user is requested to enter input regarding the patient's sitting exercise. A set icon 162 is provided for entering the number of times the patient 16 sat up. A time icon 164 is provided for entering a time period that the patient sat up, for example three minutes.

The data entered into the exercise screen 150 is sent to the controller 20, which then send the data to the remote devices 22. Accordingly, the family member 32, the caregiver 34, and the doctor/therapist are notified of the patient's progress in completing each exercise. In some embodiments, the patient's electronic medical record may also be updated with the data. After entering the data, the user may select a "back" button 170, which returns the user to the screen 140 to select another exercise. Once all of the exercise data is completed, the user may select the "finish" button 172 on screen 140 to indicate that all exercises are completed and to send the data to at least one of the devices 30, 40, and 50 or the electronic medical record.

Figure 6:
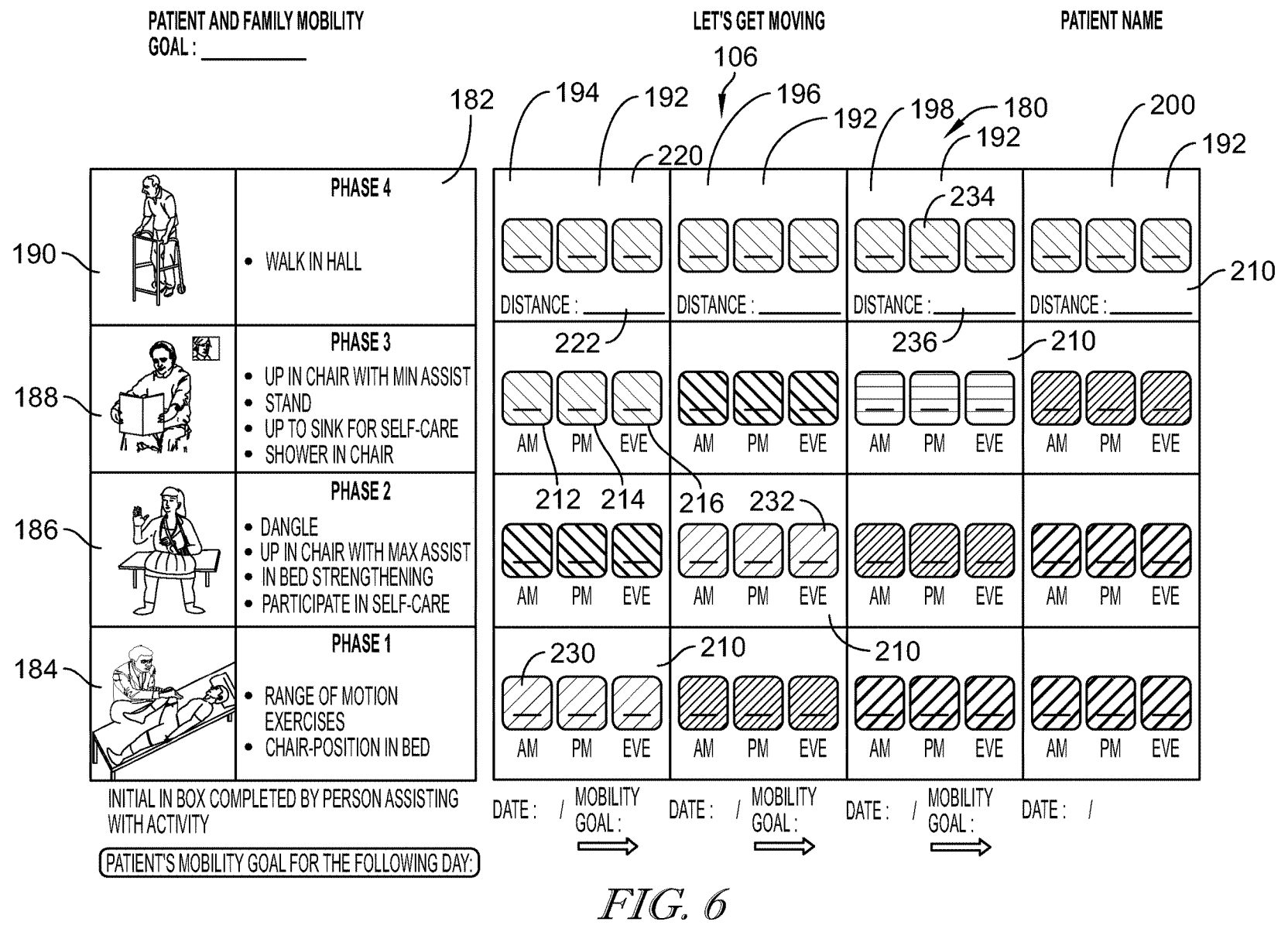

Referring to FIG. 6, a status chart 180 may be displayed on interface 106 or at least one of devices 30, 40, and 50. The status chart 180 displays the patient's progress in completing exercises. The status chart 180 includes an exercise column 182 having rows for each of phase one exercises 184, phase two exercises 186, phase three exercises 188, and phase four exercises 190. The rows are divided into columns 192 for days of the week, for example the first column 194 may be Monday, the second column 196 may be Tuesday, the third column 198 may be Wednesday, and the fourth column 200 may be Thursday, etc. Each cell 210 includes an AM box 212, a PM box 214, and an evening box 216. The boxes 212, 214, 216 are provided to check off or provide a time that the exercise was completed. In the phase four cells 220, an input 222 is also provided for tracking a distance that the patient 16 walked.

In one embodiment, if a patient 16 completed the phase one exercises at 9:00 AM on Monday, the time 9:00 AM is entered and displayed in the box 230. Further, if the patient 16 completed the phase two exercises at 10:00 PM on Tuesday, the time 10:00 PM is entered and displayed in the box 232. As another example, if the patient 16 completed the phase four exercises by walking one mile at 1:00 PM on Wednesday, the time 1:00 PM is recorded in box 234 and the distance one mile is recorded on line 236.

The status chart 180 enables the patient to track their progress with each exercise. The status chart 180 is also available for viewing by the caregiver 34, the family member 32, and/or the doctor or therapist. Accordingly, if the patient 16 is struggling to meet their exercise goals, the predetermined exercise regimen may revised to better fulfill the needs of the patient 16.

Figure 7:
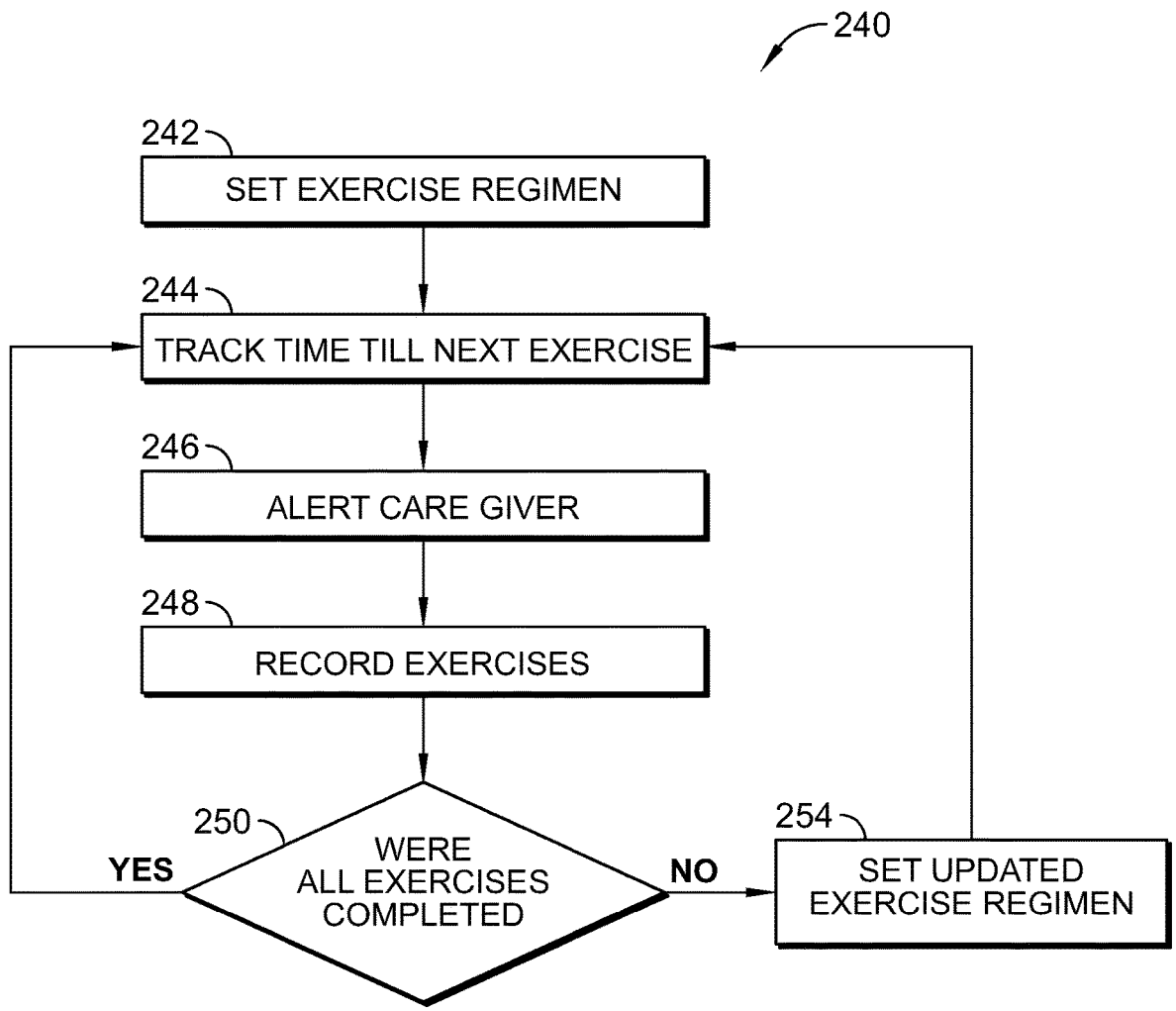
FIG. 7 is a flowchart for a method of ensuring that a patient performs daily exercise.

Referring to FIG. 7, a method 240 of ensuring the completion of patient exercise is provided. At block 242, the predetermined exercise regimen is set. The exercise regimen may be determined by a nurse, doctor, or therapist. The exercise regimen is stored in the memory 104 of the controller 20 so that exercise alerts may be delivered to the interface 106 and/or the devices 30, 40, or 50. In some embodiments, an audible alert is delivered. The controller 20 tracks the time, at block 244, and sends alerts, at block 246, when the patient 16 is required to exercise. For example, if the patient 16 is required to do phase two exercises at 10:00 AM, the screen 140 is displayed at 10:00 AM. A caregiver or family member then records the exercises performed, at block 248, using the exercise screens 100.

In some embodiments, the controller 20 may then determine whether all of the exercises were completed, at block 250. In other embodiments, a family member, caregiver, doctor, or therapist may determine whether all of the exercises were completed by viewing the status chart 180. If all of the exercises were completed, the controller 20 continues to track the time until the next exercise, at block 244.

If the exercises were not completed, the exercise regimen may be updated, at block 254. In some embodiments, the exercise regimen is updated by the caregiver, doctor, or therapist and the updated exercise regimen is saved in the memory 104. In other embodiments, the memory 104 includes an algorithm that automatically updates the exercise regimen based on the number of exercises that the patient 16 was able to complete. Once the exercise regimen is updated, the controller 20 continues to track the time until the next exercise, at block 244.

The method 240 facilitates gathering data and comparing it to pre-selected daily goals. The data is displayed to the caregiver 34 or family member 32 so that the caregiver 34 engages the family member 32. The caregiver 34 and family member 32 can then prompt the patient 16 to mobilize. The method 240 focuses on four general stages of mobility progression: 1—range of motion: head elevation, core flexibility, head turning; 2—cognitive: side-sitting within bed, vertical posture in lifts; 3—Strength: bed exits, standing at bedside, squats in bed; and 4—ambulation. The method 240 incentivizes mobility using industry-accepted mobility progression goals. The nurse is activated with mobility goal and progression to facilitate lowering the patient's length of stay in the healthcare facility 10. The method 240 also enables a physical therapist to prioritize their time in caring for numerous patients 16.

Although this disclosure refers to specific embodiments, it will be understood by those skilled in the art that various changes in form and detail may be made without departing from the subject matter set forth in the accompanying claims.

The invention claimed is:

1. A patient support apparatus comprising:
a patient support surface,
at least one load cell positioned under the patient support surface to provide signals indicative of movement of the patient on the patient support surface during an exercise regimen,
a controller having a processor and a memory, the memory having instructions stored therein related to an exercise regimen for a patient,
a graphical user interface, wherein the controller is configured to display an alert on the graphical user interface when the patient is scheduled to exercise, wherein the graphical user interface displays data related to the signals from the at least one load cell to indicate information related to exercises completed by the patient, and
user inputs displayed on the graphical user interface to enable a caregiver to record exercises completed by the patient as indicated by the signals from the at least one load cell, wherein the processor is configured to compare the exercises completed by the patient to the exercise regimen, and wherein the graphical user interface displays a chart of the exercises completed relative to the exercise regimen.

2. The apparatus of claim 1, wherein the processor is configured to update the exercise regimen based on a comparison of the exercises completed to the exercise regimen.

3. The apparatus of claim 1, wherein the controller sends an alert to a remote computer when the patient is scheduled to exercise.

4. The apparatus of claim 3, wherein the remote computer includes at least one of a computer at a nurse's station or a mobile device.

5. The apparatus of claim 1, wherein the controller sends updates to a remote computer related to the exercises completed.

6. The apparatus of claim 5, wherein the remote computer includes at least one of a nurse's computer, a doctor's computer, or a therapist's computer.

7. The apparatus of claim 1, wherein the patient support apparatus includes at least one of a hospital bed or a patient chair.

8. The apparatus of claim 1, wherein the alert includes at least one of a text message or a light.

9. The apparatus of claim 1, wherein the controller provides an audible alert when the patient is scheduled to exercise.

10. The apparatus of claim 1, wherein the graphical user interface includes a keypad to enter the exercises completed.

11. The apparatus of claim 10, wherein the keypad is a touch-screen display.

12. The apparatus of claim 1, wherein the exercise regimen includes at least one of sitting in a chair position in the patient support apparatus, range of motion exercises, participating in self-care, in-bed strengthening, sitting up in a chair with maximum assistance, dangling legs from the patient support apparatus, showering in a chair, moving to a sink for self-care, sitting up in a chair with minimum assistance, or walking.

13. The apparatus of claim 1, further comprising load cells to provide signals indicative of movement of the patient on the patient support apparatus during exercise.

14. The apparatus of claim 1, wherein the exercise regimen includes a number of sets of the exercise and a number of repetitions per set.

15. A method of using a patient support apparatus, the method comprising:
storing an exercise regimen for the patient in the memory of a controller at the patient support apparatus, the exercise regime including predetermined times for the patient to exercise,
displaying an alert on a graphical user interface at the predetermined times when the patient is scheduled to exercise,
tracking movement of the patient on a patient support surface with at least one load cell positioned under the patient support surface, wherein the movement measured is indicative of exercises completed by the patient,
recording data related to the exercises completed by the patient in the memory of the controller using user inputs displayed on the graphical user interface,
comparing the data related to the exercises completed to the exercise regimen, and
displaying on the graphical user interface a comparison of the data related to the exercises completed relative to the exercise regimen.

16. The method of claim 15, further comprising updating the exercise regimen based on the comparison of the data related to the exercises completed relative to the exercise regimen.

17. The method of claim 15, wherein the exercise regimen includes at least one of sitting in a chair position on a patient support apparatus, range of motion exercises, participating in self-care, in-bed strengthening, sitting up in a chair with maximum assistance, dangling legs from the patient support apparatus, showering in a chair, moving to a sink for self-care, sitting up in a chair with minimum assistance, or walking.

18. The method of claim 15 further comprising tracking movement of the patient based on signals from at least one load cell.

* * * * *